United States Patent
Andreu et al.

(10) Patent No.: US 12,059,635 B2
(45) Date of Patent: Aug. 13, 2024

(54) DEMULSIFIER CONTROL SYSTEM AND METHOD FOR AC/DC MODULATED DEHYDRATING AND DESALTING COALESCERS

(71) Applicant: SAUDI ARABIAN OIL COMPANY, Dhahran (SA)

(72) Inventors: Miguel Angel Lopez Andreu, Abqaiq (SA); Ramsey James White, Abqaiq (SA); Freddy Rubiano Morales, Abqaiq (SA); Sultan I. Alghamdi, Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 560 days.

(21) Appl. No.: 17/340,971

(22) Filed: Jun. 7, 2021

(65) Prior Publication Data
US 2022/0387908 A1    Dec. 8, 2022

(51) Int. Cl.
*B01D 17/12*    (2006.01)
*B01D 17/04*    (2006.01)
*G01N 33/28*    (2006.01)

(52) U.S. Cl.
CPC .......... *B01D 17/12* (2013.01); *B01D 17/047* (2013.01); *G01N 33/2823* (2013.01); *B01D 2201/54* (2013.01); *B01D 2221/04* (2013.01)

(58) Field of Classification Search
CPC .. B01D 17/12; B01D 17/047; B01D 2201/54; B01D 2221/04; G01N 33/2823
(Continued)

(56) References Cited

U.S. PATENT DOCUMENTS 7,351,320 B2 *   4/2008   Sams ................... C10G 31/08
                                                        204/663
10,513,913 B2   12/2019   Lopez et al.
(Continued)

FOREIGN PATENT DOCUMENTS

CN    201717803 U    1/2011
CN    102005937 A    4/2011
(Continued)

OTHER PUBLICATIONS

Alhajri, Nasser A. et al., "Crude Oil Process Enhancement and Water Conservation Through Industrial Revolution Initiatives"; Proceedings of the SPE Middle East Oil and Gas Show and Conference; Paper No. SPE-195044-MS; pp. 1-10; Mar. 18-21, 2019 (10 pages).
(Continued)

*Primary Examiner* — Ekandra S. Miller-Cruz
(74) *Attorney, Agent, or Firm* — Osha Bergman Watanabe & Burton LLP (57) ABSTRACT

A method of controlling a demulsifier dosage to an AC/DC modulated coalescer is described. The method includes monitoring a characteristic of an electric current drawn by an electrical component of the AC/DC modulated coalescer, determining if the characteristic of the electric current lies outside a predetermined stable range, and increasing the demulsifier dosage if the characteristic of the electric current lies outside the predetermined stable range. A system for controlling a demulsifier dosage to an AC/DC modulated coalescer with an adjustable dosing mixing valve is also described. The system includes a current sensor arranged to monitor an electric current drawn by an electrical component of the AC/DC modulated coalescer, and a processor configured to determine if a characteristic of the electric current lies outside a predetermined stable range. Furthermore, the system is configured to increase the demulsifier
(Continued)

dosage if the characteristic of the electric current lies outside the predetermined stable range.

18 Claims, 5 Drawing Sheets

(58) Field of Classification Search
USPC .......................................................... 210/708
See application file for complete search history.

(56) References Cited

U.S. PATENT DOCUMENTS

| | | | |
|---|---|---|---|
| 11,474,062 B2* | 10/2022 | Børresen | .................. C09K 8/36 |
| 2004/0094421 A1 | 5/2004 | Sams | |
| 2017/0136388 A1 | 5/2017 | Al-Shafei et al. | |
| 2018/0371876 A1 | 12/2018 | Lopez et al. | |
| 2019/0062645 A1 | 2/2019 | Al Seraihi et al. | |
| 2019/0300800 A1 | 10/2019 | Salu et al. | |
| 2020/0354640 A1 | 11/2020 | Soliman | |
| 2021/0002558 A1 | 1/2021 | Soliman et al. | |

FOREIGN PATENT DOCUMENTS

| | | |
|---|---|---|
| CN | 102061188 A | 5/2011 |
| CN | 202072669 U | 12/2011 |
| CN | 105985798 A | 10/2016 |
| WO | 2004/014512 A2 | 2/2004 |

OTHER PUBLICATIONS

Scarborough, James et al., "Minimise System Upsets in High Oil Production Facility throughout Demulsifier Chemical Trial"; Proceedings of the International Petroleum Technology Conference; Paper No. IPTC-19496-MS; pp. 1-9; Mar. 26-28, 2019 (9 pages).

* cited by examiner

DEMULSIFIER CONTROL SYSTEM AND METHOD FOR AC/DC MODULATED DEHYDRATING AND DESALTING COALESCERS

BACKGROUND

Oil and gas companies operate facilities, such as gas-oil separation plants (GOSPs), that process fluids composed of gas and produced water in addition to crude oil. One of the primary functions of a GOSP is to separate gas and water from raw crude oil to produce dry crude oil. This may be achieved by separating free gas and water using a gravity separator, such as a production trap, then using one or more AC/DC modulated coalescers, such as dehydrators and desalters, to remove emulsified brine from the crude oil. To facilitate separation and removal of the emulsified brine, a demulsifier is added to the crude oil. A demulsifier is a chemical that promotes separation of water from oil. The required amount of demulsifier in a GOSP depends on a number of factors including: crude oil composition; emulsion characteristics; vessel design; and chemical formulation of the demulsifier.

AC/DC modulated coalescers use electric fields to promote the separation of brine from oil. A minimum concentration of demulsifier is required to prevent the formation of a "rag layer" between the separated oil and brine phases in the AC/DC modulated coalescers. A rag layer comprises brine and suspended solids emulsified with crude oil. If the concentration of demulsifier is too low, rag layers are prone to grow over time and reduce the effectiveness of AC/DC modulated coalescers. Left unchecked, a growing rag layer may cause electrical short circuits when they come into contact with the electrodes of the AC/DC modulated coalescers.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to methods of controlling a demulsifier dosage to an AC/DC modulated coalescer. The method includes monitoring a characteristic of an electric current drawn by an electrical component of the AC/DC modulated coalescer, determining if the characteristic of the electric current lies outside a predetermined stable range, and increasing the demulsifier dosage if the characteristic of the electric current lies outside the predetermined stable range.

In general, in one aspect, embodiments relate to systems for controlling a demulsifier dosage to an AC/DC modulated coalescer with an adjustable dosing mixing valve. The system includes a current sensor arranged to monitor an electric current drawn by an electrical component of the AC/DC modulated coalescer, and a processor configured to determine if a characteristic of the electric current lies outside a predetermined stable range. Furthermore, the system is configured to increase the demulsifier dosage if the characteristic of the electric current lies outside the predetermined stable range.

Other aspects and advantages of the claimed subject matter will be apparent from the following description and the appended claims.

BRIEF DESCRIPTION OF DRAWINGS

Specific embodiment of the disclosed technology will now be described in detail with reference to the accompanying figures. Like elements in the various figures are denoted by like reference numerals for consistency.

DETAILED DESCRIPTION

In the following detailed description of embodiment of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

The embodiments disclosed relate to a control system and a method for controlling the demulsifier dosage upstream the HPPT, or upstream of a dehydrator, used for separating gas, oil and brine from a flow of raw crude oil to prevent excessive carryover of emulsions to the desalting train (Dehydrator and Desalter). The control system monitors characteristics of an electric current drawn by at least one electrical component energizing the AC/DC modulated coalescer. When the value of at least one characteristic of the electric current lies outside a stable range of values, indicating an elevated risk of operational upset, the demulsifier dosage is set to a higher level intended to reduce or eliminate the risk of operational upset. Conversely, when the value of at least one characteristic of the electric current lies within a stable range of values, indicating a lower risk of operational upset, the demulsifier dosage is set to a level intended to maintain operational stability of the AC/DC modulated coalescer.

Figure 1:
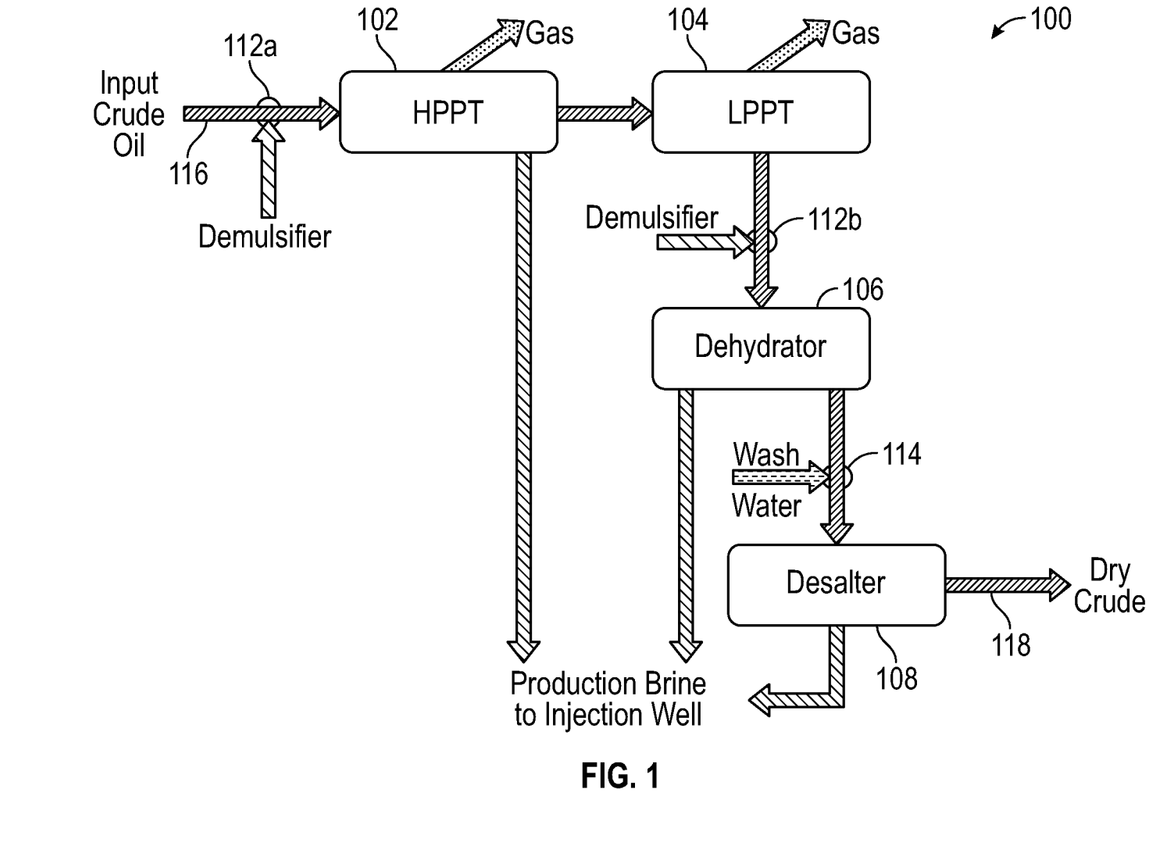
FIG. 1 shows an apparatus in accordance with one or more embodiments.

FIG. 1 shows a schematic diagram of a AC/DC modulated dehydrator/desalter gas-oil separation plant "GOSP" (100), in accordance with one or more embodiments. The GOSP (100) in this embodiment includes four major separation vessels: a high-pressure production trap "HPPT" (102); a low-pressure production trap "LPPT" (104); a dehydrator (106); and a desalter (108).

The HPPT (102) receives an input flow of raw crude oil (116) at a high pressure that is mixed with a demulsifier using an injection quill (112a). Demulsifiers, or emulsion breakers, are a class of chemicals used to separate an emulsion, including water-oil emulsion and brine-oil emulsion, into its constituent parts. The optimum dosage of demulsifier needed for raw crude oil-brine dehydration and raw crude oil desalting processes are dependent on the brine concentration, chemical composition, and temperature of the raw crude oil entering the GOSP (100). These concentrations and compositions may vary over time depending, without limitation, on changes in the flow rates of raw crude oil coming from the various oil wells contributing to the flow and the raw crude oil temperature. Optimum performance of the GOSP (100) requires continuous monitoring and adjustment of the demulsifier dosage rate to ensure a consistent and efficient separation process. The amount of demulsifier mixed with the raw crude oil may be controlled by the settings of the injection quill (112a).

A primary function of the demulsifier in the HPPT (102) is to aid in breaking the interfacial film of the emulsion (brine) droplets so that they can coalesce into larger droplets and then settle under the force of gravity. Generally, higher concentrations of the demulsifier added to the raw crude oil produce a greater degree of brine separation in the HPPT (102). This holds true up to a threshold value above which higher concentrations do not improve separation and the additional demulsifier is wasted. The percentage of water separated in the HPPT over the total produced water rate may be referred to as the "HPPT separation efficiency".

In the HPPT (102) the crude oil may separate under gravity, at least partially, into gas, a first partially separated oil, and production brine. The gas may be pumped from the HPPT (102) for further processing or use. The production brine may be pumped from the HPPT (102) for further processing or reinjection into the subsurface at an injection well.

In accordance with one or more embodiments, the first partially separated crude oil may be pumped from the HPPT (102) to an LPPT (104). At the lower pressures experienced by the first partially separated crude oil in the LPPT (104) additional gas that may have been in solution or dissolved in the first partially separated crude oil at the high pressure of the HPPT (102) may be separated from the first partially separated crude oil under gravity to produce a second partially separated crude oil. The gas may be pumped from the LPPT (104) for further processing or use.

The second partially separated crude oil pumped from the LPPT (104) may be an emulsion containing oil, brine, and suspended solids. The emulsion may be separated using a two-stage process employing AC/DC modulated coalescers. The first stage separator, or dehydrator (106) separates the brine from the emulsion, reducing the brine content of the resulting third partially separated crude oil to very low level but a high salinity. The second stage separator, or desalter (108), reduces the salinity of the third partially separated crude oil to produce dry crude oil. Both the dehydrator (106) and the desalter (108) may be AC/DC modulated coalescers, in accordance with one or more embodiments.

The second partially separated crude oil may be mixed with additional demulsifier before entering a dehydrator (106). In addition, the second partially separated crude oil may be mixed with low salinity water recycled from the desalter (108). The mixing of the demulsifier and the recycled brine may be performed using an injection quill (112b). The amount of demulsifier and recycled brine mixed with the second partially separated crude oil may be controlled by the settings of the injection quill (112b).

In the dehydrator (106) the mixed second partially separated crude oil, demulsifier, and recycled brine may be separated into a third partially separated crude oil and brine. The brine may be pumped from the dehydrator (106) for further processing or reinjection into the subsurface at an injection well. The third partially separated crude oil may be pumped from the dehydrator (106) and mixed with wash-water at a mixing valve (114). The amount of wash-water mixed with the third partially separated crude oil may be controlled by the settings of the mixing valve (114). The mixed wash-water and third partially separated crude oil may flow from the mixing valve (114) into a desalter (108).

In the desalter (108) the mixed wash-water and third partially separated crude oil may be separated into dry crude oil (118) and water. For example, the dry crude oil may have a maximum sediments and water of 0.2% and salt content of 10 pounds per thousand barrels. The dry crude oil (118) may be pumped from the desalter (108) into a pipeline and transported to another facility for further processing, such as stabilization or refining. The separated water may be injected into the subsurface at an injection well.

AC/DC modulated coalescers use electric field to promote brine separation from oil. One design of AC/DC modulated coalescers, uses direct current (DC) electric field in addition to alternating current (AC) electric fields as used in traditional designs.

Figure 2:
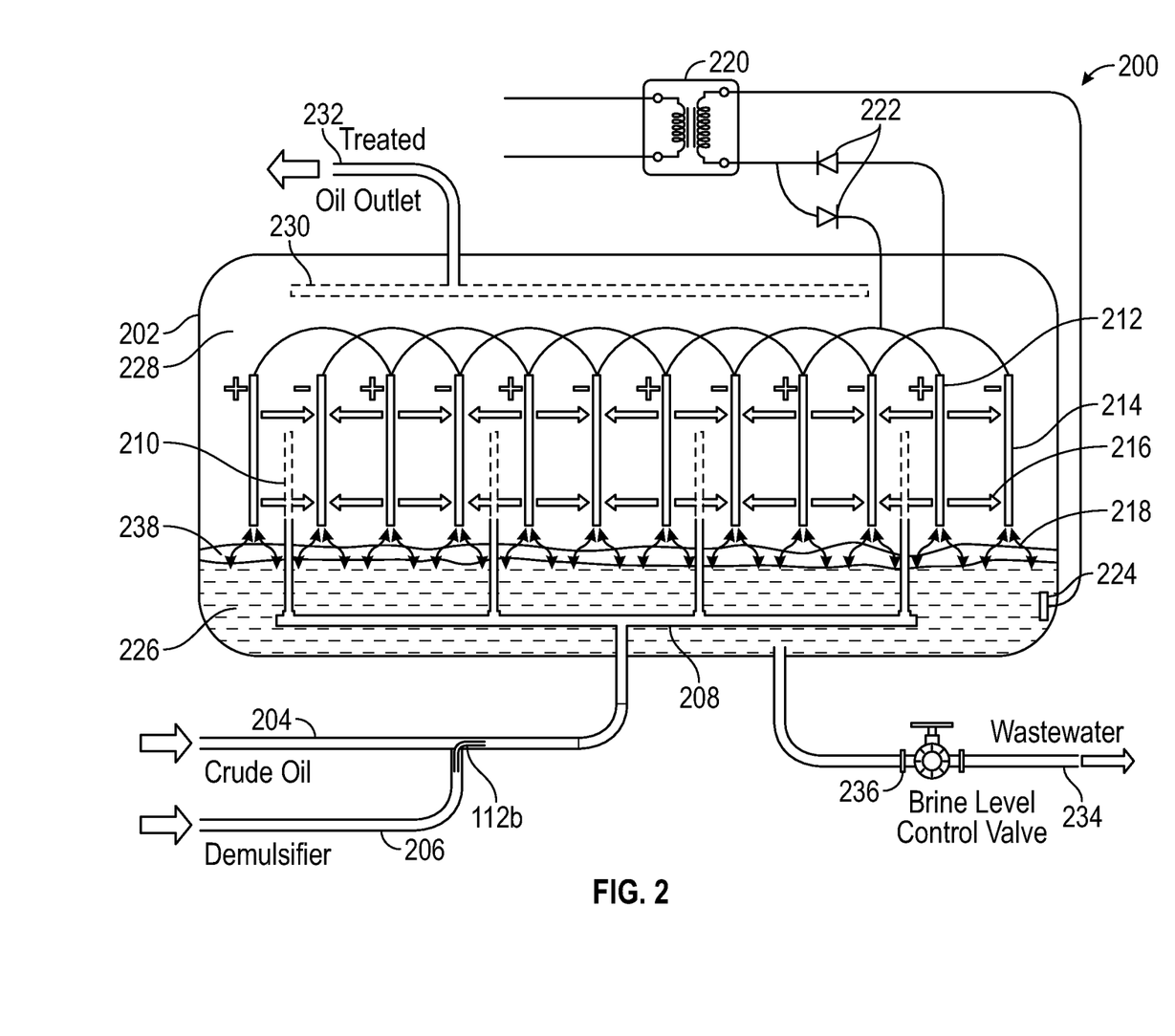
FIG. 2 shows an apparatus in accordance with one or more embodiments.

FIG. 2 depicts a dehydrator as an example of a AC/DC modulated coalescer (200), in accordance with one or more embodiments. The AC/DC modulated coalescer (200) comprises a vessel (202) into which a mixture of partially separated crude oil is fed through a first channel (204). Demulsifer is fed through a second channel (206). The demulsifier may be combined with the partially separated crude oil through an injection quill (112b) from where the mixture may flow into a crude distribution line (208). The crude distribution line (208) transports the mixture from the injection quill (112b) to crude distribution heads (210) that disperse the mixture between a plurality of positively biased electrodes (212) and a plurality of negatively biased electrodes (214).

Within the vessel (202) the mixed partially separated crude oil and demulsifier is exposed to both DC electric fields (216) between the positively biased electrodes (212) and negatively biased electrodes (214) and also AC electric fields (218) between the electrodes and a conductive brine layer (226) at the bottom of the vessel (202). At least one electrical transformer (222) may be used to energize the biased electrodes. One terminal of the electrical transformer (220) may be connected using a plurality of rectifiers (222) attached to the positively biased electrodes (212) and the negative biased electrodes (214). Another terminal of the electrical transformer (220) may be connected to a ground electrode (224) that is in electrical contact with the brine layer (226) within the vessel (202). The electrical current drawn by the transformer (220) may be measured continuously during the operation of the AC/DC modulated coalescer (200), for example using an ammeter.

Under the influence of the DC electric fields (216), the AC electric fields (218), the demulsifier, and gravity the partially separated crude oil separates into a crude oil layer (228) floating above a brine layer (226) within the vessel (202). The partially separated crude oil within the crude oil layer (228) may be extracted from the vessel (202) through a crude oil collector (230) connected to an output channel (232). Separated brine may be drained from the brine layer (226) within the vessel (202) through a wastewater channel (234). The rate at which separated brine is drained may be controlled by a brine level control valve (236)

Despite continuous demulsifier injection at the injection quill (112b), a rag layer (238) may form at the interface between the brine layer (226) and the crude oil layer (228) when the demulsifier dosage is insufficient to prevent the formation. The rag layer may include brine and suspended solids emulsified with crude oil. Failure to prevent the growth of a rag layer may result in a short-circuiting of the electrical transformer (220) when the rag layer comes into contact with the plurality of electrodes (212, 214) or, in less extreme cases, in dry crude output that does not meet the required purity specifications.

Figure 3:
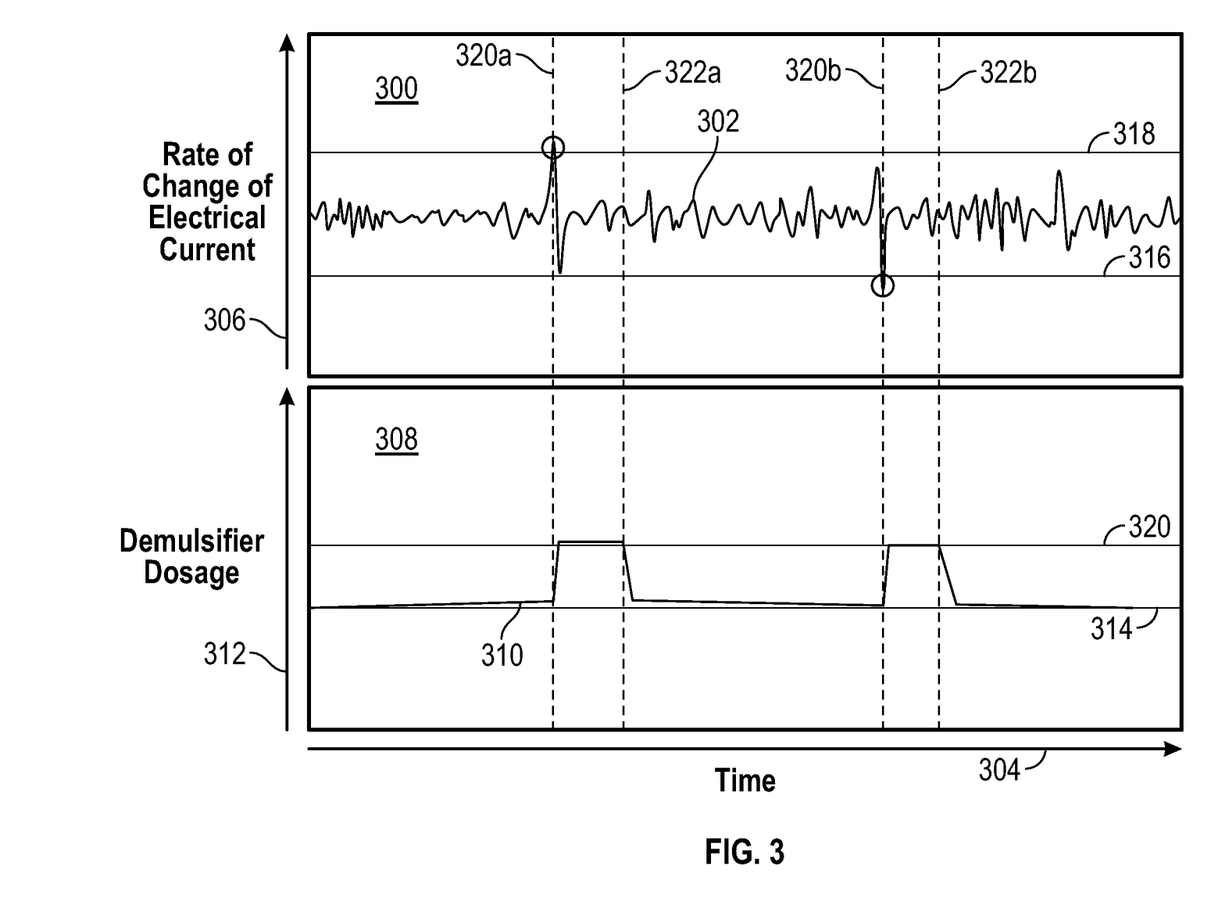
FIG. 3 shows a display of electric current change and demulisifer dosage in accordance with one or more embodiments.

FIG. 3 shows a display (300), in accordance with one or more embodiments, of the rate of change of the electrical current (302) drawn by the electrical transformer (220). Time is indicated on a horizontal axis (304) and the rate of change of electrical current is indicated on the vertical axis (306). The period of time indicated on the horizontal axis (304) may be a duration of a day or may be a greater or a lesser duration.

In accordance with one or more embodiments, FIG. 3 also shows a display of the demulsifier dosage (308) supplied at the injection quill (112b). The display (308) shows the demulsifier dosage as a function of time (310). Time is indicated on the horizontal axis (304) and the demulsifier dosage is indicated on the vertical axis (312). FIG. 3 shows a stable demulsifier dosage level (314) that produces a stable rate of change of electrical current lying in a range between a lower value (316) and an upper value (318) of the rate of change of the electrical current drawn by the electrical transformer (220). In accordance with one or more embodiments, the lower value of the rate of change of electrical current (316) may be the negative of the upper value of the rate of change of electrical current (318). Thus, the stable rate of change of electrical current may lie below an absolute value of the rate of change of electrical current.

A target demulsifier dosage may be set that promotes the efficiency of the AC/DC modulated coalescer. Generally, higher concentrations of the demulsifier mixed with the partially separate crude oil at the mixer valve prior to entry produce a greater degree of brine separation in the AC/DC modulated coalescer, e.g., the dehydrator, (106). This is true up to a threshold above which higher concentrations do not improve separation and the additional demulsifier is wasted. The target demulsifier dosage may be set to produce a stable rate of change of electrical current and a demulsifier concentration that is close to, but not greater than the threshold value. The target demulsifier dosage may depend upon the process temperature and the composition of the crude oil with water partially separated entering the AC/DC modulated coalescer, among other factors such as demulsifier effectiveness or additional shearing elements. The target rate of change of electrical current and/or the target demulsifier dosage may be set using a trial and error approach.

FIG. 3 further shows two instants in time (320a, 320b) where the value of the rate of change of the electrical current does not lie within the stable range bounded by the lower (316) and upper (318) levels. Values outside the stable range may be indicative of the formation and growth of the rag layer and, if corrective action is not taken, may be precursors to a short-circuit of the electrical transformer (220). In accordance with one or more embodiments, the appropriate corrective action in response to the rate of change of the electrical current leaving the stable range may be a rapid and significant increase in the demulsifier dosage (310) to a "disruption demulsifier dosage" level (320). The effect of increasing the demulsifier dosage (310) to a disruption demulsifier dosage level (320) is to promote the breakup of the rag layer and reduce the risk of a short-circuit of the electrical transformer (220).

In accordance with one or more embodiments, the demulsifier dosage (310) may be reduced to a stable demulsifier dosage (314) at a later time (322a, 322b) after the rag layer has dispersed and the rate of change of electrical current (302) has returned to the stable range. The demulsifier dosage (310) may remain at the stable level (314) unless and until the rate of change of electrical current (302) subsequently deviates outside the stable range at a later time.

In accordance with one or more embodiments, the parameters controlling an initiation of a change in demulsifier dosage and the rate at which the demulsifier dosage level changes may be set manually. The parameters may be set based upon experience and may be set based on a trial and error procedure. Similarly the parameters may be set based on a combination of experience and trial and error.

Figure 4:
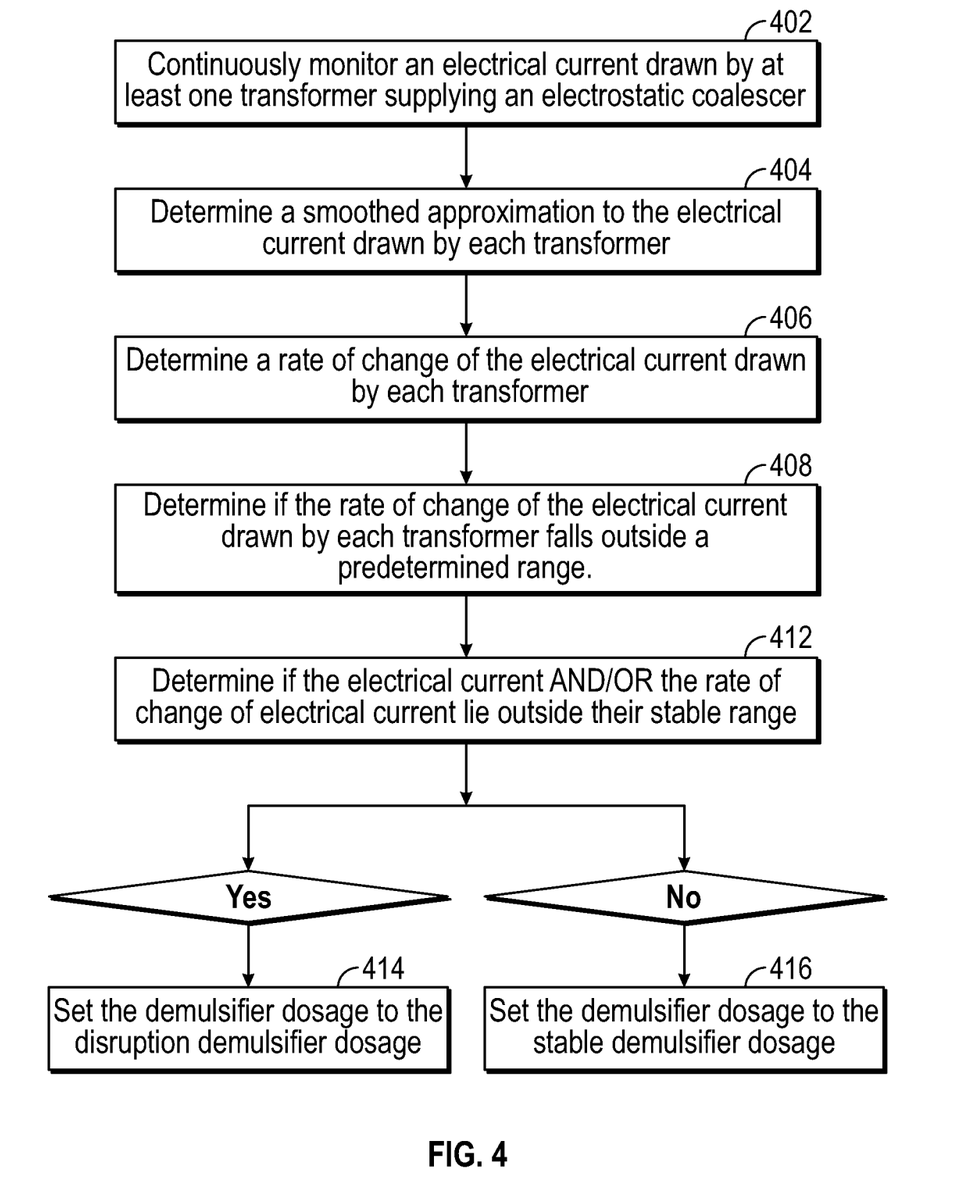
FIG. 4 shows a flowchart in accordance with one or more embodiments.

FIG. 4 shows a flowchart in accordance with one or more embodiments. In Step 402 the electrical current drawn by at least one electrical transformer (220) is monitored. In one or more embodiments, a single electrical coalescer may be include three electrical transformers, but in other embodiments there may be more or less than three. The monitoring may be continuous or may be sampled at discrete time points. The sampling at discrete time points may be performed at regular or irregular time intervals that are short compared to the temporal rate of change of the electrical current.

In Step 404 a smoothed approximation to the measured electrical current may be determined. The smooth approximation may be determined using a rolling average of the measured electrical current. The rolling average current may be determined using analog or digital filters. An analog rolling average may be implemented using an electronic low-pass filter, such as a resistor-capacitor (RC) low-pass filter or using any other low-pass analog filter familiar to one of ordinary skill art. A digital rolling average may be implemented using a convolutional box-car filter, for example, or using any other low-pass digital filter familiar to one of ordinary skill in the art. A rolling average electric current may be determined for each of the at least one electrical transformer (220) monitored in Step 402.

In Step 406 the rate of change of rolling averaged electric current may be determined, in accordance with one or more embodiments. The rate of change of rolling averaged electric current may be determined using an analogue circuit, such as a passive capacitive or passive inductive differentiator circuit. Alternatively, the rate of change of rolling averaged electric current may be determined using a digital differentiation algorithm, such as a finite difference method.

In Step 408 it may be determined if the rate of change of current drawn by the at least one transformer lies outside the stable range. In some embodiments, if the rate of change of current drawn by only one electrical transformer (220) lies outside the stable range then it is determined that a rag layer has grown to an unstable condition. In other embodiments, the rate of change of current drawn by at least two electrical transformers (220) must lie outside the stable range to indicate that a rag layer has grown to an unstable condition. In still other embodiments, the rate of change of current drawn by all electrical transformers (220) must lie outside the stable range to indicate that a rag layer may have grown to an unstable condition.

In Step 412, in accordance with one or more embodiments, if both the rate of change of the electrical current and the electric current are outside their stable range, then the demulsifier dosage may be set to a predetermined disruption demulsifier dosage in Step 414. Conversely, if either one or both of the rate of change of the electrical current and the electric current are within their stable range, then the demulsifier dosage may set to a predetermined stable demulsifier dosage in Step 416.

In Step 412, in accordance with other embodiments, if either the rate of change of the electrical current or the electric current or both are outside their stable range, then the demulsifier dosage may be set to a predetermined disruption demulsifier dosage in Step 414. Conversely, if both the rate of change of the electrical current and the electric current are within their stable range, then the demulsifier dosage may set to a predetermined stable demulsifier dosage in Step 416.

In Step 414 and Step 416 demulsifier dosage levels are set, in accordance with one or more embodiments. In some embodiments, the dosage level may be set using a proportional-integral-derivative controller (PID). A PID controller is a control loop mechanism employing feedback. A PID controller continuously calculates an error value, e(t), as the difference between a desired value, known as a "set point", in this case the desired dosage, and a measured value, known as the "process variable", in this case the current dosage. The PID controller applies a correction, i.e., a change in the dosage, based at least in part, on proportional, integral, and derivative terms of the error value. The PID controller attempts to minimize the error over time by adjustment of a control variable, u(t), such as the opening of the mixer valve to a new value determined by a weighted sum of the control terms. Mathematically u(t) may be given by:

$$u(t) = k_p\ e(t) + k_i \int_0^\tau e(t')dt' + k_d \frac{de(t)}{dt} \qquad \text{Equation (1)}$$

where $k_p$, $k_i$, and $k_d$ are tunable coefficients controlling the contributions of the proportional, integral and derivative components. The PID controller may be tuned using these three coefficients to cause the process variable to approach the set point as quickly and accurately as possible and with little or no overshoot or oscillation about the set point.

Figure 5:
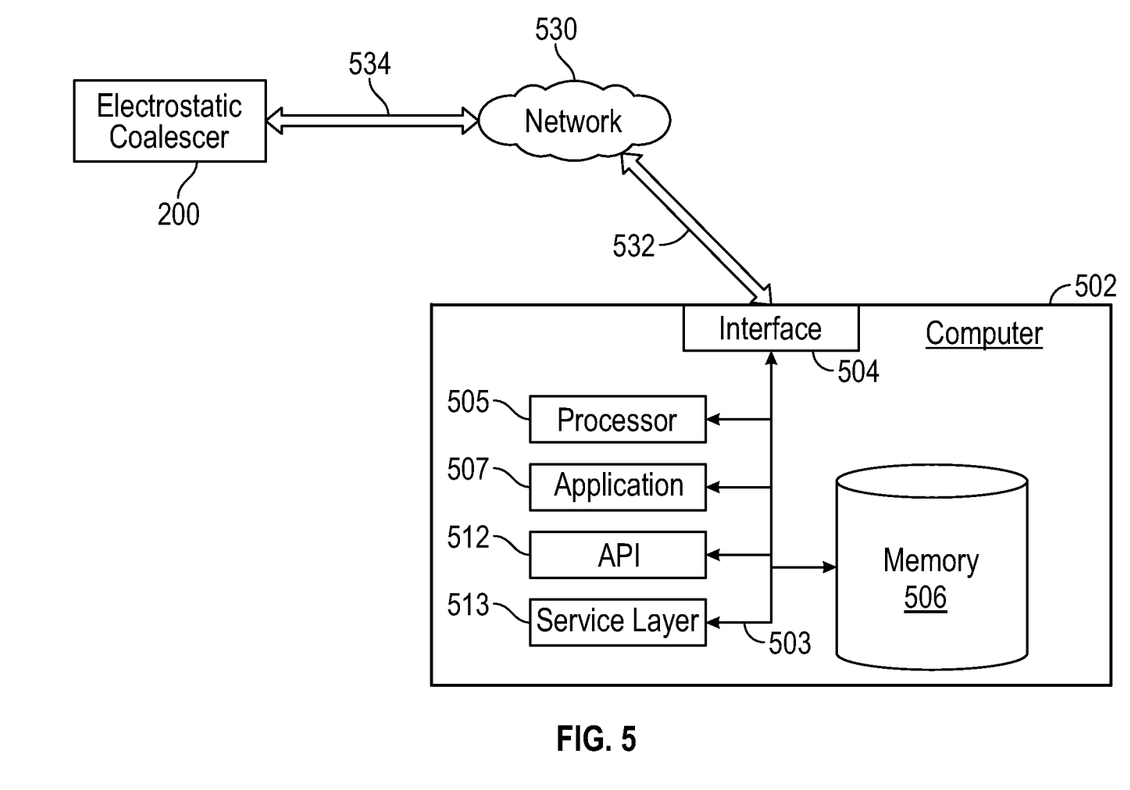
FIG. 5 shows a computer system in accordance with one or more embodiments.

FIG. 5 depicts a block diagram of a computer system (502) used to provide computational functionalities associated with described algorithms, methods, functions, processes, flows, procedures, and logic operations as described in this disclosure, according to one or more embodiments. The illustrated computer may in communication with the AC/DC Modulated coalescer (200) and may receive signals from the AC/DC Modulated coalescer (200) and send instructions to the AC/DC Modulated coalescer (200). In particular, the signals received by the computer may characterize the electrical current drawn by at least one electrical transformer (220) and the instructions sent by the computer may set the demulsifier dosage to the AC/DC Modulated coalescer (200). The signals and instructions may be sent over a network (530) that may be connected to the computer by a telecommunication channel (532) and to the AC/DC Modulated coalescer by a telecommunications channel (534).

The illustrated computer (502) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (502) may include a computer that includes an input device, such as a keypad, keyboard, touch screen, or other device that can accept user information, and an output device that conveys information associated with the operation of the computer (502), including digital data, visual, or audio information (or a combination of information), or a graphical user interface (GUI).

The computer (502) can serve in a role as a client, network component, a server, a database or other persistency, or any other component (or a combination of roles) of a computer system for performing the subject matter described in the instant disclosure. The illustrated computer (502) is communicably coupled with a network (530). In some implementations, one or more components of the computer (502) may be configured to operate within environments, including cloud-computing-based, local, global, or other environment (or a combination of environments).

At a high level, the computer (502) is an electronic computing device operable to receive, transmit, process, store, or manage data and information associated with the described subject matter. According to some implementations, the computer (502) may also include or be communicably coupled with an application server, e-mail server, web server, caching server, streaming data server, business intelligence (BI) server, or other server (or a combination of servers).

The computer (502) can receive requests over network (530) from a client application (for example, executing on another computer (502)) and responding to the received requests by processing the said requests in an appropriate software application. In addition, requests may also be sent to the computer (502) from internal users (for example, from a command console or by other appropriate access method), external or third-parties, other automated applications, as well as any other appropriate entities, individuals, systems, or computers.

Each of the components of the computer (502) can communicate using a system bus (503). In some implementations, any or all of the components of the computer (502), both hardware or software (or a combination of hardware and software), may interface with each other or the interface (504) (or a combination of both) over the system bus (503) using an application programming interface (API) (512) or a service layer (513) (or a combination of the API (512) and service layer (513). The API (512) may include specifications for routines, data structures, and object classes. The API (512) may be either computer-language independent or dependent and refer to a complete interface, a single function, or even a set of APIs. The service layer (513) provides software services to the computer (502) or other components (whether or not illustrated) that are communicably coupled to the computer (502). The functionality of the computer (502) may be accessible for all service consumers using this service layer. Software services, such as those provided by the service layer (513), provide reusable, defined business functionalities through a defined interface. For example, the interface may be software written in JAVA, C++, or other suitable language providing data in extensible markup language (XML) format or another suitable format. While illustrated as an integrated component of the computer (502), alternative implementations may illustrate the API (512) or the service layer (513) as stand-alone components in relation to other components of the computer (502) or other components (whether or not illustrated) that are communicably coupled to the computer (502). Moreover, any or all parts of the API (512) or the service layer (513) may be implemented as child or sub-modules of another software module, enterprise application, or hardware module without departing from the scope of this disclosure.

The computer (502) includes an interface (504). Although illustrated as a single interface (504) in FIG. 5, two or more interfaces (504) may be used according to particular needs, desires, or particular implementations of the computer (502). The interface (504) is used by the computer (502) for communicating with other systems in a distributed environment that are connected to the network (530). Generally, the interface (504 includes logic encoded in software or hardware (or a combination of software and hardware) and operable to communicate with the network (530). More specifically, the interface (504) may include software supporting one or more communication protocols associated with communications such that the network (530) or interface's hardware is operable to communicate physical signals within and outside of the illustrated computer (502).

The computer (502) includes at least one computer processor (505). Although illustrated as a single computer processor (505) in FIG. 5, two or more processors may be used according to particular needs, desires, or particular implementations of the computer (502). Generally, the computer processor (505) executes instructions and manipulates data to perform the operations of the computer (502) and any algorithms, methods, functions, processes, flows, and procedures as described in the instant disclosure.

The computer (502) also includes a memory (506) that holds data for the computer (502) or other components (or a combination of both) that can be connected to the network (530). For example, memory (506) can be a database storing data consistent with this disclosure. Although illustrated as a single memory (506) in FIG. 5, two or more memories may be used according to particular needs, desires, or particular implementations of the computer (502) and the described functionality. While memory (506) is illustrated as an integral component of the computer (502), in alternative implementations, memory (506) can be external to the computer (502).

The application (507) is an algorithmic software engine providing functionality according to particular needs, desires, or particular implementations of the computer (502), particularly with respect to functionality described in this disclosure. For example, application (507) can serve as one or more components, modules, applications, etc. Further, although illustrated as a single application (507), the application (507) may be implemented as multiple applications (507) on the computer (502). In addition, although illustrated as integral to the computer (502), in alternative implementations, the application (507) can be external to the computer (502).

There may be any number of computers (502) associated with, or external to, a computer system containing computer (502), wherein each computer (502) communicates over network (530). Further, the term "client," "user," and other appropriate terminology may be used interchangeably as appropriate without departing from the scope of this disclosure. Moreover, this disclosure contemplates that multiple users may use one computer (502), or that one user may use multiple computers (502).

Although only a few example embodiments have been described in detail above, those skilled in the art will readily appreciate that many modifications are possible in the example embodiment without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed is:

1. A method of controlling a demulsifier dosage to prevent growth of a rag layer comprising brine and suspended solids emulsified with crude oil, in an AC/DC modulated coalescer, comprising:
    monitoring a characteristic of an electric current drawn by an electrical component of the AC/DC modulated coalescer;
    determining a stable range of the characteristic, wherein the characteristic lying within the stable range indicates absence of the rag layer and wherein the characteristic lying outside the stable range indicates presence of the rag layer;
    setting the demulsifier dosage to a stable demulsifier dosage when the characteristic lies within the stable range;
    setting the demulsifier dosage to a disruption demulsifier dosage when the characteristic lies outside the stable range; and
    controlling the demulsifer dosage, comprising:
        raising the demulsifier dosage to the disruption demulsifier dosage or
        reducing the demulsifier dosage to the stable demulsifier dosage.

2. The method of claim 1, further comprising setting a target separation efficiency for the AC/DC modulated coalescer based, at least in part, on the characteristic.

3. The method of claim 1, wherein setting the demulsifier dosage to a disruption demulsifier dosage is based, at least in part, on a combination of the characteristic, an integral of the characteristic, and a derivative of the characteristic.

4. The method of claim 1, wherein the characteristic comprises a rate of change of magnitude of the electric current.

5. The method of claim 1, wherein the characteristic comprises a magnitude of the electric current.

6. The method of claim 2, wherein setting the target separation efficiency comprises determining the stable demulsifier dosage.

7. The method of claim 6, wherein determining the stable demulsifier dosage comprises determining a target demulsifier dosage required to achieve a stable value of the characteristic.

8. The method of claim 2, wherein setting the target separation efficiency comprises determining an operating temperature of the AC/DC modulated coalescer.

9. The method of claim 1, wherein the AC/DC modulated coalescer comprises a dehydrator or a desalter.

10. A non-transitory computer readable medium storing instructions executable by a computer processor for controlling a demulsifier dosage to prevent growth of a rag layer comprising brine and suspended solids emulsified with crude oil, the instructions comprising functionality for:

monitoring a characteristic of an electric current drawn by an electrical component of an AC/DC modulated coalescer;

determining a stable range of the characteristic, wherein the characteristic lying within the stable range indicates absence of a rag layer and wherein the characteristic lying outside the stable range indicates presence of a rag layer;

setting a demulsifier dosage to a stable demulsifier dosage when the characteristic lies within the stable range;

setting the demulsifier dosage to a disruption demulsifier dosage when the characteristic lies outside the stable range; and         controlling the demulsifer dosage, comprising:

raising the demulsifier dosage to the disruption demulsifier dosage or             reducing the demulsifier dosage to the stable demulsifier dosage.

11. The non-transitory computer readable medium of claim 10, the instructions further comprising functionality for setting a target separation efficiency for the AC/DC modulated coalescer based, at least in part, on the characteristic.

12. A system for controlling a demulsifier dosage to prevent growth of a rag layer comprising brine and suspended solids emulsified with crude oil, in an AC/DC modulated coalescer having an adjustable dosing mixing valve, the system comprising:

a current sensor arranged to monitor an electric current drawn by an electrical component of the AC/DC modulated coalescer; and     a processor configured to:

determine a characteristic of the electric current;

determine a stable range of the characteristic, wherein the characteristic lying within the stable range indicates absence of the rag layer and wherein the characteristic lying outside the stable range indicates presence of the rag layer;

set the demulsifier dosage to a stable demulsifier dosage when the characteristic lies within the stable range;

set the demulsifier dosage to a disruption demulsifier dosage when the characteristic lies outside the stable range; and         control the demulsifier dosage, comprising:

instructing the adjustable dosing mixing valve to increase the demulsifier dosage to the disruption demulsifier dosage or             instructing the adjustable dosing mixing valve to reduce the demulsifier dosage to the stable demulsifier dosage.

13. The system of claim 12, wherein the stable range is determined based on a target separation efficiency for the AC/DC modulated coalescer.

14. The system of claim 12, wherein the characteristic comprises a rate of change of magnitude of the electric current.

15. The system of claim 12, wherein the characteristic comprises a magnitude of the electric current.

16. The system of claim 12, wherein the stable demulsifier dosage is determined based on the demulsifier dosage required to achieve a desired value of the characteristic.

17. The system of claim 13, wherein the target separation efficiency is based, at least in part, on an operating temperature of the AC/DC modulated coalescer.

18. The system of claim 12, wherein the AC/DC modulated coalescer comprises a dehydrator or a desalter.

* * * * *